(12) United States Patent
Brenner

(10) Patent No.: US 6,518,023 B1
(45) Date of Patent: Feb. 11, 2003

(54) METHOD OF MAPPING RESTRICTION SITES IN POLYNUCLEOTIDES

(75) Inventor: Sydney Brenner, Cambridge (GB)

(73) Assignee: Lynx Therapeutics, Inc., Hayward, CA (US)

( * ) Notice: Subject to any disclaimer, the term of this patent is extended or adjusted under 35 U.S.C. 154(b) by 0 days.

(21) Appl. No.: 09/446,081

(22) PCT Filed: Jun. 25, 1998

(86) PCT No.: PCT/US98/13335

§ 371 (c)(1),
(2), (4) Date: Mar. 27, 2000

(87) PCT Pub. No.: WO99/00519

PCT Pub. Date: Jan. 7, 1999

Related U.S. Application Data

(63) Continuation-in-part of application No. 08/884,189, filed on Jun. 27, 1997, now abandoned.

(51) Int. Cl.[7] .............................. C12Q 1/68; C12M 1/34; C07H 21/04; G01N 33/00

(52) U.S. Cl. ............................ 435/6; 435/6; 435/91.1; 435/183; 435/287.2; 436/94; 536/23.1; 536/24.3

(58) Field of Search .......................... 435/6, 91.1, 183, 435/287.2; 436/94; 536/23.1, 24.3

(56) References Cited

U.S. PATENT DOCUMENTS

| 5,102,785 A | 4/1992 | Livak et al. |
| 5,552,278 A | 9/1996 | Brenner |
| 5,599,675 A | 2/1997 | Brenner |
| 5,604,097 A | 2/1997 | Brenner |
| 5,695,934 A | 12/1997 | Brenner |
| 5,846,719 A | 12/1998 | Brenner et al. |
| 5,858,671 A | * 1/1999 | Jones .......................... 435/6 |

OTHER PUBLICATIONS

Dynal, "Dnyabeads Template Preparation Kit" product advertisement, (1991).
International Search Report for Application No. PCT/US98/13335.

* cited by examiner

*Primary Examiner*—B. L. Sisson
(74) *Attorney, Agent, or Firm*—Vincent M. Powers; LeeAnn Gorthey

(57) ABSTRACT

The invention provides a method for constructing a high resolution physical map of a polynucleotide. In accordance with the invention, the polynucleotide is digested successively with at least two different restriction endonucleases and the ends of the restriction fragments are sequenced after each digestion. In this manner, restriction fragments having sequenced ends are produced that can be aligned by their sequences to give a physical map of the polynucleotide. Preferably, restriction fragment ends are sequenced by massively parallel signature sequencing (MPSS), or a like parallel sequencing technique.

13 Claims, 5 Drawing Sheets

Multiple 'e' recognition sites between consecutive 'r' sites

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
      (A) LENGTH: 20 nucleotides
      (B) TYPE: nucleic acid
      (C) STRANDEDNESS: double
      (D) TOPOLOGY: linear (xi) SEQUENCE DESCRIPTION: SEQ ID NO: 1:

AGAATTCGGG CCTTAATTAA     20

(2) INFORMATION FOR SEQ ID NO: 2:

(i) SEQUENCE CHARACTERISTICS:
        (A) LENGTH: 20 nucleotides
        (B) TYPE: nucleic acid
        (C) STRANDEDNESS: double
        (D) TOPOLOGY: linear (xi) SEQUENCE DESCRIPTION: SEQ ID NO: 2:

```
GGGTACCAAG TCAGAGTGAT                                            20
```

(2) INFORMATION FOR SEQ ID NO: 3:

(i) SEQUENCE CHARACTERISTICS:
        (A) LENGTH: 18 nucleotides
        (B) TYPE: nucleic acid
        (C) STRANDEDNESS: double
        (D) TOPOLOGY: linear (xi) SEQUENCE DESCRIPTION: SEQ ID NO: 3:

```
GATCCTTAAT TAAGAGCT                                              18
```

(2) INFORMATION FOR SEQ ID NO: 4:

(i) SEQUENCE CHARACTERISTICS:
        (A) LENGTH: 22 nucleotides
        (B) TYPE: nucleic acid
        (C) STRANDEDNESS: double
        (D) TOPOLOGY: linear (xi) SEQUENCE DESCRIPTION: SEQ ID NO: 4:

```
CTAGAAGCTG CGCTTGCTTT TG                                         22
```

(2) INFORMATION FOR SEQ ID NO: 5:

(i) SEQUENCE CHARACTERISTICS:
        (A) LENGTH: 19 nucleotides
        (B) TYPE: nucleic acid
        (C) STRANDEDNESS: double
        (D) TOPOLOGY: linear (xi) SEQUENCE DESCRIPTION: SEQ ID NO: 5:

```
GAATTCGGGC CTTAATTAA                                             19
```

(2) INFORMATION FOR SEQ ID NO: 6:

(i) SEQUENCE CHARACTERISTICS:
        (A) LENGTH: 19 nucleotides
        (B) TYPE: nucleic acid
        (C) STRANDEDNESS: double
        (D) TOPOLOGY: linear (xi) SEQUENCE DESCRIPTION: SEQ ID NO: 6:

```
CAAAAGCAAG CGCAGCTTC                                             19
```

(2) INFORMATION FOR SEQ ID NO: 7:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO: 7:

```
AGAATTCGGG CCTTAATTAA                                            20
```

(2) INFORMATION FOR SEQ ID NO: 8:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO: 8:

ATCACTCTGA CTTGGTACCC                                                     20

(2) INFORMATION FOR SEQ ID NO: 9:

(i) SEQUENCE CHARACTERISTICS:
        (A) LENGTH: 44 nucleotides
        (B) TYPE: nucleic acid
        (C) STRANDEDNESS: double
        (D) TOPOLOGY: linear (xi) SEQUENCE DESCRIPTION: SEQ ID NO: 9:

AATTTGTCGA CATCTTCTCT TGGTACCGAA TTCAAATTTC TGCA                  44

(2) INFORMATION FOR SEQ ID NO: 10:

(i) SEQUENCE CHARACTERISTICS:
        (A) LENGTH: 19 nucleotides
        (B) TYPE: nucleic acid
        (C) STRANDEDNESS: double
        (D) TOPOLOGY: linear (xi) SEQUENCE DESCRIPTION: SEQ ID NO: 10

GTCGACGGGC CTTAATTAA                                                       19

(2) INFORMATION FOR SEQ ID NO: 11:

(i) SEQUENCE CHARACTERISTICS:
        (A) LENGTH: 19 nucleotides
        (B) TYPE: nucleic acid
        (C) STRANDEDNESS: double
        (D) TOPOLOGY: linear (xi) SEQUENCE DESCRIPTION: SEQ ID NO: 11:

ACGTACGGAC GTCTTTAAA                                                       19

(2) INFORMATION FOR SEQ ID NO: 12:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 12:

ANNNTACAGC TGCATCCCTT GGCGCTGAGG                              30

(2) INFORMATION FOR SEQ ID NO: 13:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 13:

NANNTACAGC TGCATCCCTG GGCCTGTAAG                              30

(2) INFORMATION FOR SEQ ID NO: 14:

(i) SEQUENCE CHARACTERISTICS:
            (A) LENGTH: 30 nucleotides
            (B) TYPE: nucleic acid
            (C) STRANDEDNESS: double
            (D) TOPOLOGY: linear (xi) SEQUENCE DESCRIPTION: SEQ ID NO: 14:

CNNNTACAGC TGCATCCCTT GACGGGTCTC                                              30

(2) INFORMATION FOR SEQ ID NO: 15:

(i) SEQUENCE CHARACTERISTICS:
            (A) LENGTH: 30 nucleotides
            (B) TYPE: nucleic acid
            (C) STRANDEDNESS: double
            (D) TOPOLOGY: linear (xi) SEQUENCE DESCRIPTION: SEQ ID NO: 15:

NCNNTACAGC TGCATCCCTG CCCGCACAGT                                              30

(2) INFORMATION FOR SEQ ID NO: 16:

(i) SEQUENCE CHARACTERISTICS:
            (A) LENGTH: 30 nucleotides
            (B) TYPE: nucleic acid
            (C) STRANDEDNESS: double
            (D) TOPOLOGY: linear (xi) SEQUENCE DESCRIPTION: SEQ ID NO: 16:

GNNNTACAGC TGCATCCCTT CGCCTCGGAC                                              30

(2) INFORMATION FOR SEQ ID NO: 17:

(i) SEQUENCE CHARACTERISTICS:
            (A) LENGTH: 30 nucleotides
            (B) TYPE: nucleic acid
            (C) STRANDEDNESS: double
            (D) TOPOLOGY: linear (xi) SEQUENCE DESCRIPTION: SEQ ID NO: 17:

NGNNTACAGC TGCATCCCTG ATCCGCTAGC                                              30

(2) INFORMATION FOR SEQ ID NO: 18:

(i) SEQUENCE CHARACTERISTICS:
            (A) LENGTH: 30 nucleotides
            (B) TYPE: nucleic acid
            (C) STRANDEDNESS: double
            (D) TOPOLOGY: linear (xi) SEQUENCE DESCRIPTION: SEQ ID NO: 18:

TNNNTACAGC TGCATCCCTT CCGAACCCGC                                              30

(2) INFORMATION FOR SEQ ID NO: 19:

(i) SEQUENCE CHARACTERISTICS:
            (A) LENGTH: 30 nucleotides
            (B) TYPE: nucleic acid
            (C) STRANDEDNESS: double
            (D) TOPOLOGY: linear (xi) SEQUENCE DESCRIPTION: SEQ ID NO: 19:

NTNNTACAGC TGCATCCCTG AGGGGGATAG                                              30

(2) INFORMATION FOR SEQ ID NO: 20

(i) SEQUENCE CHARACTERISTICS:
    (A) LENGTH: 30 nucleotides
    (B) TYPE: nucleic acid
    (C) STRANDEDNESS: double
    (D) TOPOLOGY: linear (xi) SEQUENCE DESCRIPTION: SEQ ID NO: 20:

NNANTACAGC TGCATCCCTT CCCGCTACAC                    30

(2) INFORMATION FOR SEQ ID NO: 21:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 21:

NNNATACAGC TGCATCCCTG ACTCCCCGAG                    30

(2) INFORMATION FOR SEQ ID NO: 22:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 22:

NNCNTACAGC TGCATCCCTG TGTTGCGCGG                    30

(2) INFORMATION FOR SEQ ID NO: 23:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 23:

NNNCTACAGC TGCATCCCTC TACAGCAGCG                    30

(2) INFORMATION FOR SEQ ID NO: 24:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 24:

NNGNTACAGC TGCATCCCTG TCGCGTCGTT                    30

(2) INFORMATION FOR SEQ ID NO: 25:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 25:

NNNGTACAGC TGCATCCCTC GGAGCAACCT                    30

(2) INFORMATION FOR SEQ ID NO: 26:

(i) SEQUENCE CHARACTERISTICS:

-continued

```
       (A) LENGTH: 30 nucleotides
       (B) TYPE: nucleic acid
       (C) STRANDEDNESS: double
       (D) TOPOLOGY: linear (xi) SEQUENCE DESCRIPTION: SEQ ID NO: 26:

NNTNTACAGC TGCATCCCTG GTGACCGTAG                                  30

(2) INFORMATION FOR SEQ ID NO: 27:

(i) SEQUENCE CHARACTERISTICS:
       (A) LENGTH: 30 nucleotides
       (B) TYPE: nucleic acid
       (C) STRANDEDNESS: double
       (D) TOPOLOGY: linear (xi) SEQUENCE DESCRIPTION: SEQ ID NO: 27:

NNNTTACAGC TGCATCCCTC CCCTGTCGGA                                  30
```

METHOD OF MAPPING RESTRICTION SITES IN POLYNUCLEOTIDES

This is a continuation-in-part of U.S. patent application Ser. No. 08/884,189 filed Jun. 27, 1997, now abandoned, which is incorporated herein by reference.

FIELD OF THE INVENTION

The invention relates generally to methods for construction physical maps of genomic DNA, and more particularly, to a method of providing high resolution physical maps using a parallel DNA sequencing technology, such as massively parallel signature sequencing (MPSS).

BACKGROUND

Physical maps of one or more large pieces of DNA, such as a genome or chromosome, consist of an ordered collection of molecular landmarks that may be used to position, or map, a smaller fragment, such as clone containing a gene of interest, within the larger structure, e.g. U.S. Department of Energy, "Primer on Molecular Genetics," from Human Genome 1991–92 Program Report; and Los Alamos Science, 20: 112–122 (1992). An important goal of the Human Genome Project has been to provide a series of genetic and physical maps of the human genome with increasing resolution, i.e. with reduced distances in basepairs between molecular landmarks, e.g. Murray et al, Science, 265: 2049–2054 (1994); Hudson et al, Science, 270: 1945–1954 (1995); Schuler et al, Science, 274: 540–546 (1996); and so on. Such maps have great value not only in furthering our understanding of genome organization, but also as tools for helping to fill contig gaps in large-scale sequencing projects and as tools for helping to isolate disease-related genes in positional cloning projects, e.g. Rowen et al, pages 167–174, in Adams et al, editors, Automated DNA Sequencing and Analysis (Academic Press, New York, 1994); Collins, Nature Genetics, 9: 347–350 (1995); Rossiter and Caskey, Annals of Surgical Oncology, 2: 14–25 (1995); and Schuler et al (cited above). In both cases, the ability to rapidly construct high-resolution physical maps of large pieces of genomic DNA is highly desirable.

Two important approaches to genomic mapping include the identification and use of sequence tagged sites (STS's), e.g. Olson et al, Science, 245: 1434–1435 (1989); and Green et al, PCR Methods and Applications, 1: 77–90 (1991), and the construction and use of jumping and linking libraries, e.g. Collins et al, Proc. Natl. Acad. Sci., 81: 6812–6816 (1984); and Poustka and Lehrach, Trends in Genetics, 2: 174–179 (1986). The former approach makes maps highly portable and convenient, as maps consist of ordered collections of nucleotide sequences that allow application without having to acquire scarce or specialized reagents and libraries. The latter approach provides a systematic means for identifying molecular landmarks spanning large genetic distances and for ordering such landmarks via hybridization assays with members of a linking library.

Unfortunately, these approaches to mapping genomic DNA are difficult and laborious to implement. It would be highly desirable if there was an approach for constructing physical maps that combined the systematic quality of the jumping and linking libraries with the convenience and portability of the STS approach.

SUMMARY OF THE INVENTION

Accordingly, an object of my invention is to provide a method for constructing high resolution physical maps of genomic DNA.

Another object of my invention is to provide a method mapping genomic DNA by massively parallel signature sequencing of restriction fragments of the genomic DNA.

Another object of my invention is to provide a method of ordering restriction fragments by aligning matching sequences of their ends.

A further object of my invention is to provide physical maps of genomic DNA that consist of an ordered collection of nucleotide sequences spaced at an average distance of a few kilobases or less.

My invention achieves these and other objects by providing a method for constructing a physical map of a polynucleotide. In accordance with the invention, a polynucleotide is digested successively with at least two different restriction endonucleases and the ends of the restriction fragments are sequenced after each digestion. In this manner, restriction fragments having sequenced ends are produced that can be aligned by their sequences to give a physical map of the polynucleotide. Preferably, restriction fragment ends are sequenced by massively parallel signature sequencing (MPSS), or a like parallel sequencing technique.

DEFINITIONS

Figure 1A:
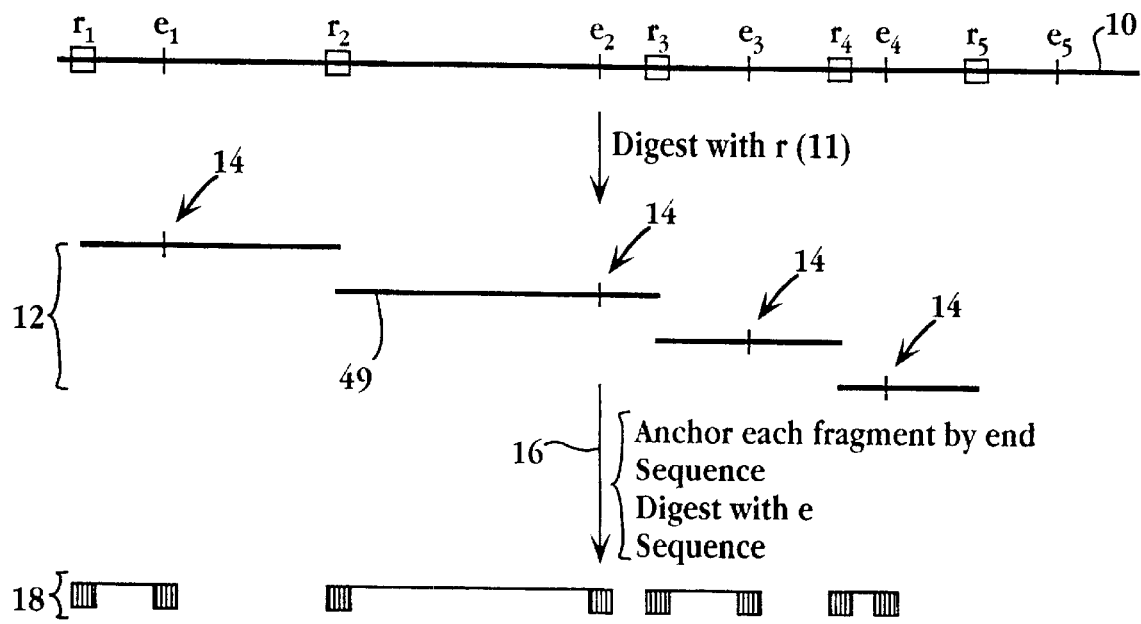
FIGS. 1A–1D graphically illustrate the concept of the invention.

As used herein, the term "ligation" means the formation of a covalent bond between the ends of one or more (usually two) oligonucleotides. The term usually refers to the formation of a phosphodiester bond resulting from the following reaction, which is usually catalyzed by a ligase:

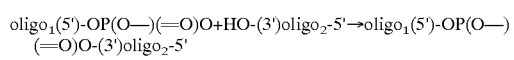

where $oligo_1$ and $oligo_2$ are either two different oligonucleotides or different ends of the same oligonucleotide. The term encompasses non-enzymatic formation of phosphodiester bonds, as well as the formation of non-phosphodiester covalent bonds between the ends of oligonucleotides, such as phosphorothioate bonds, disulfide bonds, and the like. A ligation reaction is usually template driven, in that the ends of $oligo_1$ and $oligo_2$ are brought into juxtaposition by specific hybridization to a template strand. A special case of template-driven ligation is the ligation of two double stranded oligonucleotides having complementary protruding strands.

"Complement" or "tag complement" as used herein in reference to oligonucleotide tags refers to an oligonucleotide to which a oligonucleotide tag specifically hybridizes to form a perfectly matched duplex or triplex. In embodiments where specific hybridization results in a triplex, the oligonucleotide tag may be selected to be either double stranded or single stranded. Thus, where triplexes are formed, the term "complement" is meant to encompass either a double stranded complement of a single stranded oligonucleotide tag or a single stranded complement of a double stranded oligonucleotide tag.

The term "oligonucleotide" as used herein includes linear oligomers of natural or modified monomers or linkages, including deoxyribonucleosides, ribonucleosides, anomeric forms thereof, peptide nucleic acids (PNAs), and the like, capable of specifically binding to a target polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 3–4, to several tens of monomeric units, e.g. 40–60. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. Usually oligonucleotides of the invention comprise the four natural nucleotides; however, they may also comprise non-natural nucleotide analogs. It is clear to those skilled in the art when oligonucleotides having natural or non-natural nucleotides may be employed, e.g. where processing by enzymes is called for, usually oligonucleotides consisting of natural nucleotides are required.

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex. Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen bonding.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g described by Scheit, Nucleotide Analogs (John Wiley, New York, 1980); Uhlman and Peyman, Chemical Reviews, 90: 543–584 (1990), or the like, with the only proviso that they are capable of specific hybridization. Such analogs include synthetic nucleosides designed to enhance binding properties, reduce complexity, increase specificity, and the like.

As used herein "sequence determination" or "determining a nucleotide sequence" in reference to polynucleotides includes determination of partial as well as full sequence information of the polynucleotide. That is, the term includes sequence comparisons, fingerprinting, and like levels of information about a target polynucleotide, as well as the express identification and ordering of nucleosides, usually each nucleoside, in a target polynucleotide. The term also includes the determination of the identification, ordering, and locations of one, two, or three of the four types of nucleotides within a target polynucleotide. For example, in some embodiments sequence determination may be effected by identifying the ordering and locations of a single type of nucleotide, e.g. cytosines, within the target polynucleotide "CATCGC . . . " so that its sequence is represented as a binary code, e.g. "100101 . . . " for "C—(not C)—(not C)—C—(not C)—C . . . " and the like.

As used herein, the term "complexity" in reference to a population of polynucleotides means the number of different species of polynucleotide present in the population.

DETAILED DESCRIPTION OF THE INVENTION

In accordance with the present invention, nucleotide sequences at the ends of restriction fragments are used to order the fragments into a physical map. Preferably, a target polynucleotide is digested with at least two different restriction endonucleases (or at least one restriction endonuclease and its cognate methylase), after which the ends of the resulting fragments are sequenced.

Figure 1B:
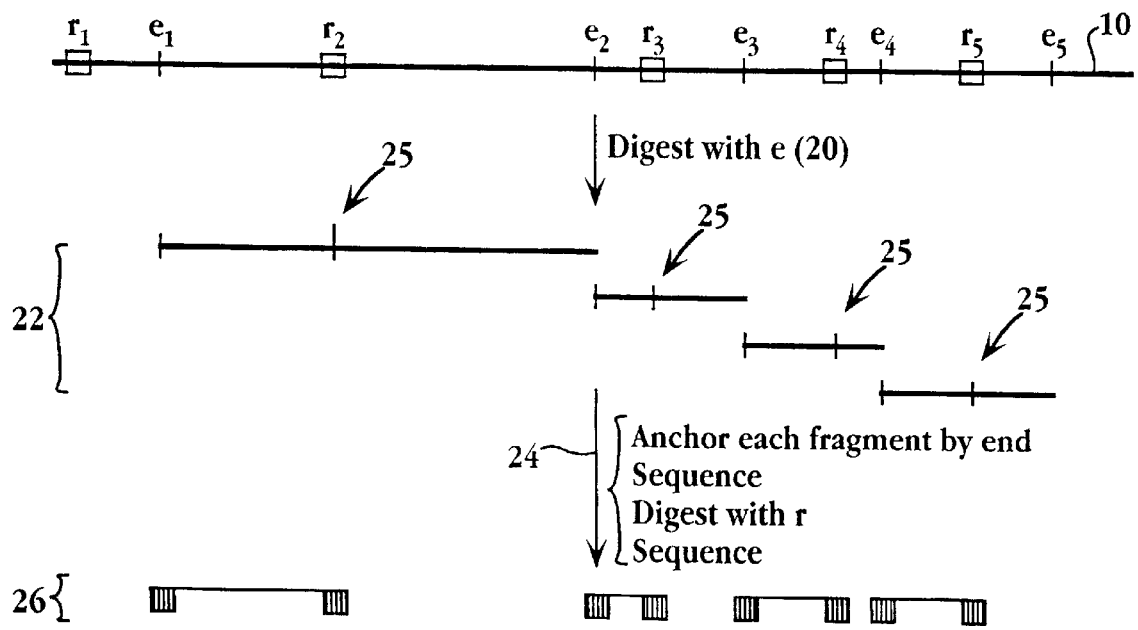
Figure 1C:
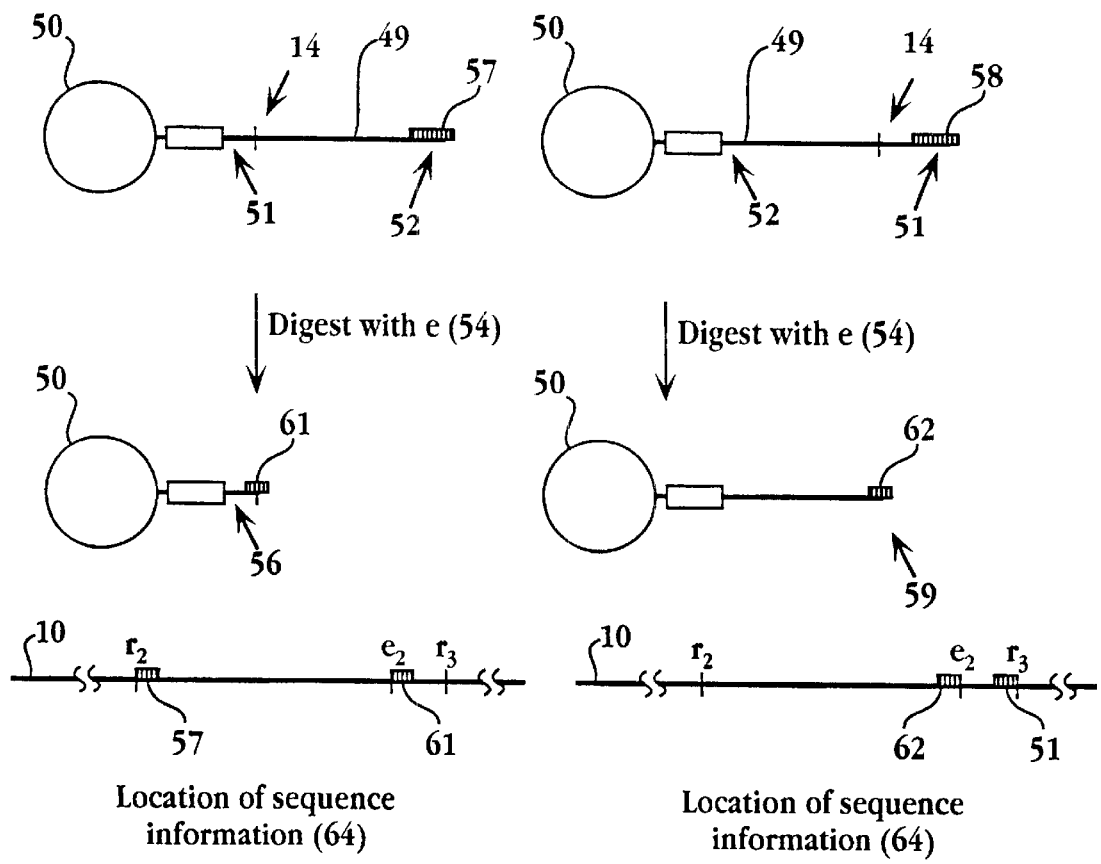

The concept of the invention may be illustrated by considering the ideal situation of FIG. 1A, where polynucleotide (10) has recognition sites ($r_1$, $r_2$, $r_3$, $r_4$, and $r_5$) for restriction endonucleases r and recognition sites ($e_1$ through $e_5$) for restriction endonuclease e, such that the sites of the two restriction endonucleases alternate. That is, between any two consecutive sites for r there is exactly one site for e, and between any two consecutive sites for e there is exactly one site for r. A sample of polynucleotide (10) is digested with r (11) to produce fragments (12), each of the fragments having a single recognition site (14) for e. As illustrated in FIG. 1C and described in more detail below, each fragment, e.g. (49), is preferably anchored by an end (51) to a solid phase support (50), after which the nucleotide sequence (57) of the free end (52) is determined. Of course, any nucleotide sequencing method can be employed, but as explained more fully below, the most useful application of the invention can be made when a technique is employed that permits many thousands of fragments to be sequenced at the same time.

Once the sequence of each free end (52) is obtained, the fragments are digested (54) with e, and the nucleotide sequence (61) of new free end (56) is determined. In the preferred embodiment, this process is carried out on each fragment in both orientations with respect to which end is anchored to the solid phase support as a result of the sequencing approach employed, although such "double" sequencing is not necessary for the invention. It is merely a consequence of the use of MPSS to determine the sequences. That is, separately, fragment (49) is anchored by end (52) and the nucleotide sequence (58) of free end (51) is determined, after which fragment (49) is digested with e to produce new free end (59). The nucleotide sequence (62) of the new free end (59) is then determined. The locations (64) of the sequence elements (51), (57), (61), and (62) are summarized at the bottom of FIG. 1C.

A consequence of the "over-determination" of sequence information by MPSS is that two independent physical maps are produced simultaneously. Generally, one map consists of the sequences on one side of each restriction cleavage, and the other map consists of the sequences on the other side of each restriction cleavage.

Figure 1D:
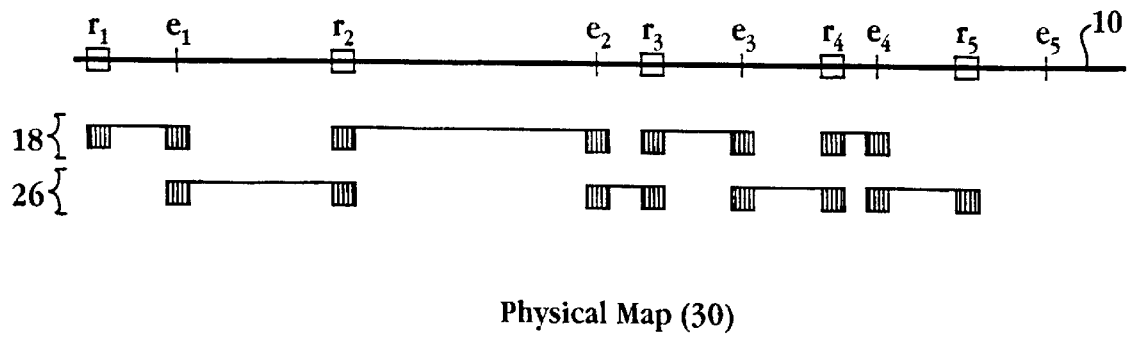

Returning to FIGS. 1A and 1B, the locations of the ordered pairs of sequences (18) of the fragments (12) and their relative positions are illustrated. However, the ordered pairs are not linked. Linking information is obtained by digesting another sample of polynucleotide (10) with e (20)

to form fragments (22), each of which has a single recognition site (25) for r. Ordered pairs of sequences (26) are obtained, after processing fragments (22) as fragments (12) were processed, with the exception that the second digestion is with r. If ordered pairs (26) are combined with ordered pairs (18), as shown in FIG. 1D, a physical map (30) is obtained.

Figure 2:
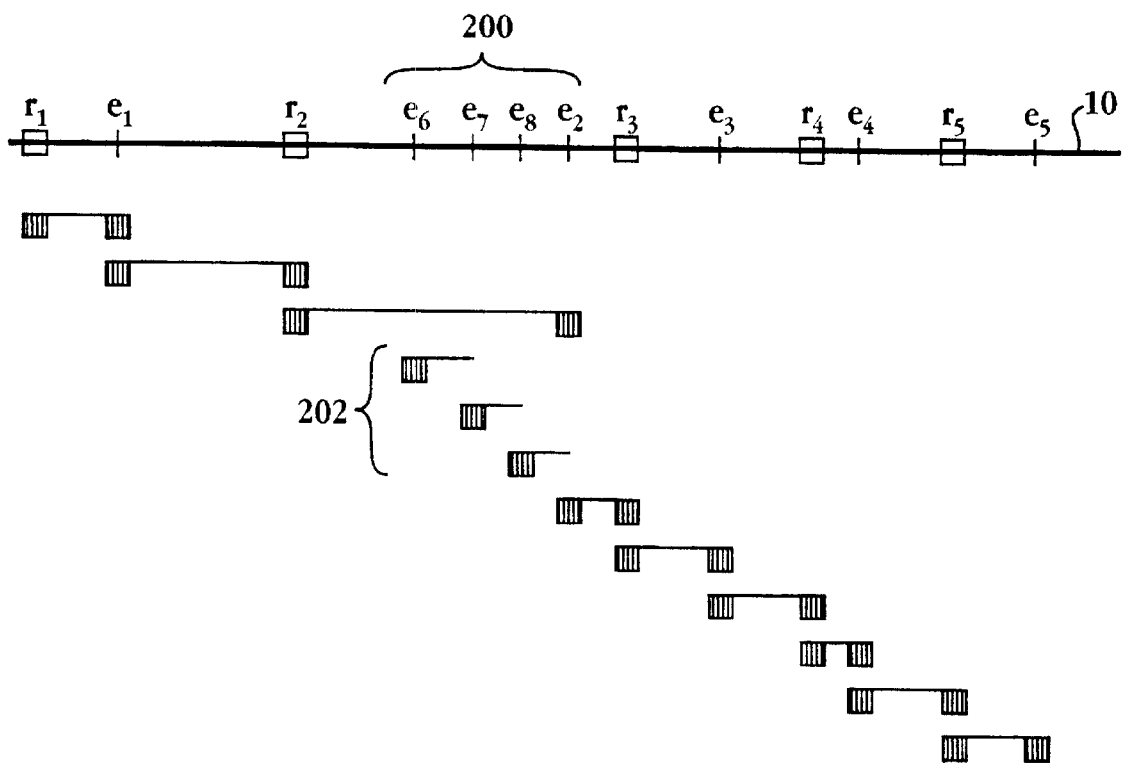
FIG. 2 illustrates the effect of the occurrence of multiple restriction recognition sites of a second restriction endonuclease between two consecutive restriction recognition sites of a first restriction endonuclease.

As illustrated by polynucleotide (10') of FIG. 2, when multiple recognition sites (200), e.g. $e_6$, $e_7$, $e_8$, and $e_2$, of one of the restriction endonucleases occurs between two consecutive recognition sites of the other restriction endonuclease, some fragments (202) will not give rise to ordered pairs of sequences. Such sequences can simply be ignored when ordered pairs are assembled into a physical map.

In many cases, a pattern of recognition sites of two or more restriction endonucleases may be converted into the alternating pattern of FIGS. 1A–1D by constructing jumping and linking libraries. This is especially in the case where at least one restriction endonuclease is a "rare cutter" and the rest are "frequent cutters," e.g. as for a restriction endonuclease with a 6- or 8-basepair recognition sequence and those with a 4-basepair recognition sequence, respectively. Jumping and linking libraries also allow sequence analysis of shorter fragments when one of the restriction endonuclease give rise to unmanageably large fragments with respect to the sequencing technique employed. Preferably, for MPSS the fragment should be less than a few kilobases in length; more preferably, they should be less than 2 kilobases in length; and still more preferably, the fragments should be less than 1.5 kilobases in length.

Preferably, jumping and linking libraries are prepared as described by in the following references: Collins et al, Proc. Natl. Acad. Sci., 81: 6812–6816 (1984); Poustka and Lehrach, Genetic Engineering, 10: 169–193 (1988); and Poustka and Lehrach, Trends in Genetics, 2: 174179 (1986). Briefly, a first and a second restriction endonuclease are selected so that the second restriction endonuclease cleaves a polynucleotide much more frequently than the first restriction endonuclease, e.g. the first restriction endonuclease may recognize a six-basepair sequence and the second restriction endonuclease may recognize a four-basepair sequence. Preferably, the second restriction endonuclease is selected so that there is at least one recognition site for the second restriction endonuclease between every two consecutive recognition sites of the first restriction endonuclease. The polynucleotide is digested with the first restriction endonuclease, after which the restriction fragments are re-ligated at low concentration in the presence of a selectable marker, so that single-fragment circles with a selectable marker are the predominant ligation product. The ligation products are digested with the second restriction endonuclease and the resulting fragments are inserted into a first cloning vector. The selectable marker must not contain recognition sites of the second endonuclease. Clones selected by the marker form a jumping library, so-named because the inserts of the clones contain sequences adjacent to consecutive recognition sites of the first restriction endonuclease and of the immediately neighboring recognition sites of the second restriction endonuclease, but every thing else has been deleted, or "jumped" over, effectively resulting in a configuration of alternating recognition sites, similar to that of FIGS. 1A–1D.

Separately the polynucleotide is digested with the second endonuclease, after which the restriction fragments are re-ligated at low concentration in the presence of a selectable marker, again so that single-fragment circles with a selectable marker are the predominant ligation product. Clones selected by the marker form a linking library, so-named because the inserts of the clones contain sequences adjacent to recognition sites of the second restriction endonuclease immediately upstream and downstream of a recognition site of the first restriction endonuclease; thus, it has sequences common to, or "linking," consecutive recognition sites of the first restriction endonuclease.

Once the jumping and linking libraries are constructed, a physical map may be made by excising the inserts of the first and second plasmids and by carrying out the process described for the embodiment of FIGS. 1A–1D; namely, tagging, cloning, sampling, and sorting, in accordance with Brenner et al. (cited below), followed by sequencing, digesting, and sequencing to form ordered pairs of sequences, which are assembled into a physical map.

The number of nucleotides identified in the regions adjacent to each restriction site depends on the size of the polynucleotide being mapped and the number of fragments generated by the restriction digests. Preferably, a sufficient number of nucleotides are identified so that each of the determined sequences is unique, so as to avoid ambiguous solutions when ordered pairs are assembled into a physical map. Thus, for cosmid-sized polynucleotides cleaved with a restriction endonuclease that recognizes a four basepair sequence (a "4-cutter"), about 160 ($\approx$40,000/256) fragments are produced on average, so the number of nucleotides determined could be as low as five. If the target polynucleotide is a bacterial genome of 1 megabase for the same restriction endonuclease, about 4000 fragments are generated (or about 8000 ends) and the number of nucleotides determined could be as low as seven, and still have a significant probability that each end sequence would be unique. Preferably, for polynucleotides less than or equal to 10 megabases, at least 9 nucleotides are determined in the regions adjacent to restriction sites, when a 4-cutter restriction endonuclease is employed. Generally for polynucleotides less than or equal to 10 megabases, 12–18 nucleotides are preferably determined to ensure that the end sequences are unique. For polynucleotides greater than 10 megabases, from 18–24 nucleotides are preferably determined.

Determination of Restriction Fragment Sequences by Massively Parallel Signature Sequencing (MPSS)

Preferably, ordered pairs of sequences are obtained from restriction fragments by MPSS, which is a combination of two techniques: one for tagging and sorting fragments of DNA for parallel processing (e.g. Brenner et al., PCT Pubn. No. WO 96/41011), and another for the stepwise sequencing of the end of a DNA fragment (e.g. Brenner, U.S. Pat. No. 5,599,675). After an initial digestion of a target polynucleotide with a first restriction endonuclease, restriction fragments are ligated to oligonucleotide tags as described below, and in Brenner et al., PCT Pubn. No. WO 96/41011, so that the resulting tag-fragment conjugates may be sampled, amplified, and sorted onto separate solid phase supports by specific hybridization of the oligonucleotide tags with their tag complements.

Once an amplified sample of fragments is sorted onto solid phase supports to form homogeneous populations of substantially identical fragments, the ends of the fragments are preferably sequenced with an adaptor-based method of DNA sequencing that includes repeated cycles of ligation, identification, and cleavage, such as the method described in Brenner, U.S. Pat. No. 5,599,675. In further preference, adaptors used in the sequencing method each have a protruding strand and an oligonucleotide tag selected from a minimally cross-hybridizing set of oligonucleotides (described more fully below). Such adaptors are referred to herein as "encoded adaptors." Encoded adaptors whose protruding strands form perfectly matched duplexes with the complementary protruding strands of a fragment are ligated. After ligation, the identity and ordering of the nucleotides in the protruding strand is determined, or "decoded," by specifically hybridizing a labeled tag complement, or "decoder" to its corresponding tag on the ligated adaptor.

The preferred sequencing method is carried out with the following steps: (a) ligating an encoded adaptor to an end of a fragment, the encoded adaptor having a nuclease recognition site of a nuclease whose cleavage site is separate from its recognition site; (b) identifying one or more nucleotides at the end of the fragment by the identity of the encoded adaptor ligated thereto; (c) cleaving the fragment with a nuclease recognizing the nuclease recognition site of the encoded adaptor such that the fragment is shortened by one or more nucleotides; and (d) repeating said steps (a) through (c) until said nucleotide sequence of the end of the fragment is determined. In the identification step, successive sets of tag complements, or "de-coders," are specifically hybridized to the respective tags carried by encoded adaptors ligated to the ends of the fragments. The type and sequence of nucleotides in the protruding strands of the polynucleotides are identified by the label carried by the specifically hybridized de-coder and the set from which the de-coder came, as described below.

Oligonucleotide Tags and Tag Complements

Oligonucleotide tags are employed for two different purposes in the preferred embodiments of the invention: Oligonucleotide tags are employed as described in Brenner, U.S. Pat. No. 5,604,097; and PCT Pubn. No. WO 96/41011, to sort large numbers of polynucleotides, e.g. several thousand to several hundred thousand, from a mixture into uniform populations of identical polynucleotides for analysis, and they are employed to deliver labels to encoded adaptors that number in the range of a few tens to a few thousand. For the former use, large numbers, or repertoires, of tags are typically required, and therefore synthesis of individual oligonucleotide tags is problematic. In these embodiments, combinatorial synthesis of the tags is preferred. On the other hand, where extremely large repertoires of tags are not required—such as for delivering labels to encoded adaptors, oligonucleotide tags of a minimally cross-hybridizing set may be separately synthesized, as well as synthesized combinatorially.

Sets containing several hundred to several thousands, or even several tens of thousands, of oligonucleotides may be synthesized directly by a variety of parallel synthesis approaches, e.g. as disclosed in Frank et al., U.S. Pat. No. 4,689,405; Frank et al., Nucleic Acids Research 11: 4365–4377 (1983); Matson et al., Anal. Biochem. 224: 110–116 (1995); Fodor et al., PCT Pubn. No. WO 93/22684; Pease et al., Proc. Natl. Acad. Sci. 91: 5022–5026 (1994); Southern et al., J. Biotechnology 35: 217–227 (1994), Brennan, PCT Pubn. No. WO 94/27719; Lashkari et al., Proc. Natl. Acad. Sci. 92: 7912–7915 (1995); or the like.

Preferably, tag complements in mixtures, whether synthesized combinatorially or individually, are selected to have similar duplex or triplex stabilities to one another so that perfectly matched hybrids have similar or substantially identical melting temperatures. This permits mis-matched tag complements to be more readily distinguished from perfectly matched tag complements when applied to encoded adaptors, e.g. by washing under stringent conditions. For combinatorially synthesized tag complements, minimally cross-hybridizing sets may be constructed from subunits that make approximately equivalent contributions to duplex stability as every other subunit in the set. Guidance for carrying out such selections is provided by published techniques for selecting optimal PCR primers and calculating duplex stabilities, e.g. Rychlik et al, Nucleic Acids Research, 17: 8543–8551 (1989) and 18: 6409–6412 (1990); Breslauer et al, Proc. Natl. Acad. Sci., 83: 3746–3750 (1986); Wetmur, Crit. Rev. Biochem. Mol. Biol., 26: 227–259 (1991); and the like. When smaller numbers of oligonucleotide tags are required, such as for delivering labels to encoded adaptors, the computer programs of Appendices I and II may be used to generate and list the sequences of minimally cross-hybridizing sets of oligonucleotides that are used directly (i.e. without concatenation into "sentences"). Such lists can be further screened for additional criteria, such as GC-content, distribution of mismatches, theoretical melting temperature, and the like, to form additional minimally cross-hybridizing sets.

For shorter tags, e.g. about 30 nucleotides or less, the algorithm described by Rychlik and Wetmur is preferred for calculating duplex stability, and for longer tags, e.g. about 30–35 nucleotides or greater, an algorithm disclosed by Suggs et al, pages 683–693 in Brown, editor, ICN-UCLA Symp. Dev. Biol., Vol. 23 (Academic Press, New York, 1981) may be conveniently employed. Clearly, there are many approaches available to one skilled in the art for designing sets of minimally cross-hybridizing subunits within the scope of the invention. For example, to minimize the affects of different base-stacking energies of terminal nucleotides when subunits are assembled, subunits may be provided that have the same terminal nucleotides. In this way, when subunits are linked, the sum of the base-stacking energies of all the adjoining terminal nucleotides will be the same, thereby reducing or eliminating variability in tag melting temperatures.

The oligonucleotide tags of the invention and their complements are conveniently synthesized on an automated DNA synthesizer, e.g. an Applied Biosystems, Inc. (Foster City, Calif.) model 392 or 394 DNA/RNA Synthesizer, using standard chemistries, such as phosphoramidite chemistry, e.g. disclosed in the following references: Beaucage and Iyer. Tetrahedron, 48: 2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like.

Oligonucleotide tags for sorting may range in length from 12 to 60 nucleotides or basepairs. Preferably, oligonucleotide tags range in length from 18 to 40 nucleotides or basepairs. More preferably, oligonucleotide tags range in length from 25 to 40 nucleotides or basepairs. In terms of preferred and more preferred numbers of subunits, these ranges may be expressed as follows:

TABLE III

Numbers of Subunits in Tags in Preferred Embodiments

| Monomers in Subunit | Nucleotides in Oligonucleotide Tag | | |
|---|---|---|---|
| | (12–60) | (18–40) | (25–40) |
| 3 | 4–20 subunits | 6–3 subunits | 8–13 subunits |
| 4 | 3–15 subunits | 4–10 subunits | 6–10 subunits |

TABLE III-continued

Numbers of Subunits in Tags in Preferred Embodiments

| Monomers in Subunit | Nucleotides in Oligonucleotide Tag | | |
|---|---|---|---|
| | (12–60) | (18–40) | (25–40) |
| 5 | 2–12 subunits | 3–8 subunits | 5–8 subunits |
| 6 | 2–10 subunits | 3–6 subunits | 4–6 subunits |

Most preferably, oligonucleotide tags for sorting are single stranded and specific hybridization occurs via Watson-Crick pairing with a tag complement.

Preferably, repertoires of single stranded oligonucleotide tags for sorting contain at least 100 members; more preferably, repertoires of such tags contain at least 1000 members; and most preferably, repertoires of such tags contain at least 10,000 members.

Preferably, repertoires of tag complements for delivering labels contain at least 16 members; more preferably, repertoires of such tags contain at least 64 members. Still more preferably, such repertoires of tag complements contain from 16 to 1024 members, e.g. a number for identifying nucleotides in protruding strands of from 2 to 5 nucleotides in length. Most preferably, such repertoires of tag complements contain from 64 to 256 members. Repertoires of desired sizes are selected by directly generating sets of words, or subunits, of the desired size, e.g. with the help of the computer programs of disclosed by Brenner et al (cited above), or repertoires are formed generating a set of words which are then used in a combinatorial synthesis scheme to give a repertoire of the desired size. Preferably, the length of single stranded tag complements for delivering labels is between 8 and 20. More preferably, the length is between 9 and 15.

In embodiments where specific hybridization occurs via triplex formation, coding of tag sequences follows the same principles as for duplex-forming tags; however, there are further constraints on the selection of subunit sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. There is extensive guidance in the literature for selecting appropriate sequences, orientation, conditions, nucleoside type (e.g. whether ribose or deoxyribose nucleosides are employed), base modifications (e.g. methylated cytosine, and the like) in order to maximize, or otherwise regulate, triplex stability as desired in particular embodiments. Conditions for annealing single-stranded or duplex tags to their single-stranded or duplex complements are well known, e.g. Ji et al, Anal. Chem. 65: 1323–1328 (1993). Cantor et al, U.S. Pat. No. 5,482,836; and the like. Use of triplex tags in sorting has the advantage of not requiring a "stripping" reaction with polymerase to expose the tag for annealing to its complement.

An exemplary tag library for sorting is constructed as follows. A mixture of 8-word tags of nucleotides A, G, and T are chemically synthesized in accordance with the formula:

$$3'\text{-AATT-}[^4(A,C,T)_8]\text{-CCCT}_p$$

where "$[^4(A,G,T)_8]$" indicates a tag mixture where each tag consists of eight 4-mer words of A, G, and T; and "p" indicate a 5' phosphate. This mixture is ligated to the following right and left primer binding regions (SEQ ID NO: 1 & 2):

```
5'- AGAATTCGGGCCTTAATTAA    5'- GGGTACCAAGTCAGAGTGAT
    TCACCGACCCGGAATTp           TGGTTCAGTCTCACTA

LEFT                        RIGHT
```

The right and left primer binding regions are ligated to the above tag mixture, after which the single stranded portion of the ligated structure is filled with DNA polymerase then mixed with the right and left primers indicated below and amplified to give a tag library.

Formula I

```
         Left Primer                         Kpn I

5'- AGAATTCGGGCCTTAATTAA                       ↓

5'- AGAATTCGGGCCTTAATTAA-  [4(A,C,T)8]-GGGTACCAAGTCAGAGTGAT
    TCTTAAGCCCGGAATTAATT-  [4(T,G,A)8]-CCCATGGTTCAGTCTCACTA

↑              ↑                   CCCATGGTTCAGTCTCACTA -5'

Eco RI         Pac I                        Right Primer
```

The flanking regions of the oligonucleotide tag may be engineered to contain restriction site, as exemplified above, for convenient insertion into and excision from cloning vectors. Optionally, the right or left primers may be synthesized with a biotin attached (using conventional reagents, e.g. available from Clontech Laboratories, Palo Alto, Calif.) to facilitate purification after amplification and/or cleavage. Preferably, for making tag-fragment conjugates, the above library is inserted into a conventional cloning vector, such a pUC19, or the like.

A general method for exposing the single stranded tag involves digesting tag-fragment conjugates with the 5'→3' exonuclease activity of T4 DNA polymerase, or a like enzyme. When used in the presence of a single deoxynucleoside triphosphate, such a polymerase will cleave nucleotides from 3' ends present on the non-template strand of a double stranded fragment until a complement of the single deoxynucleoside triphosphate is reached on the template strand. When such a nucleotide is reached the 5'→3' digestion effectively ceases, as the polymerase's extension activity adds nucleotides at a higher rate than the excision activity removes nucleotides. Consequently, single stranded tags constructed with three nucleotides are readily prepared for loading onto solid phase supports.

The technique may also be used to preferentially methylate interior IIs sites of a fragment while leaving a single IIs site at the terminus of the fragment unmethylated. First, the terminal IIs site is rendered single stranded using a polymerase with, e.g., deoxycytidine triphosphate. The double stranded portion of the fragment is then methylated, after which the single stranded terminus is filled in with a DNA polymerase in the presence of all four nucleoside triphosphates, thereby regenerating the IIs site.

Use of Encoded Adaptors for Base-by-base Sequencing

Preferably, encoded adaptors are used in the sequencing method described in Brenner U.S. Pat. No. 5,599,675. Each encoded adaptor comprises a protruding strand and an oligonucleotide tag selected from a minimally cross-hybridizing set of oligonucleotides. Encoded adaptors whose protruding strands form perfectly matched duplexes with the complementary protruding strands of the target polynucleotide are ligated. After ligation, the identity and ordering of the nucleotides in the protruding strands are determined, or "decoded," by specifically hybridizing a labeled tag complement to its corresponding tag on the ligated adaptor. As used herein, the term "de-coder" refers to labeled tag complements used in connection with encoded adaptors.

For example, if an encoded adaptor with a protruding strand of four nucleotides, say 5'-AGGT, forms a perfectly matched duplex with the complementary protruding strand of a target polynucleotide and is ligated, the four complementary nucleotides, 3'-TCCA, on the polynucleotide may be identified by a unique oligonucleotide tag selected from a set of 256 such tags, one for every possible four nucleotide sequence of the protruding strands. Tag complements are applied to the ligated adaptors under conditions which allow specific hybridization of only those tag complements that form perfectly matched duplexes (or triplexes) with the oligonucleotide tags of the ligated adaptors. The tag complements may be applied individually or as one or more mixtures to determine the identity of the oligonucleotide tags, and therefore, the sequences of the protruding strands.

Encoded adaptors can have several embodiments depending, for example, on whether single or double stranded tags are used, whether multiple tags are used, whether a 5' protruding strand or 3' protruding strand is employed, whether a 3' blocking group is used, and the like. Formulas for several embodiments of encoded adaptors are shown below. Preferred structures for encoded adaptors using one single stranded tag are as follows:

or

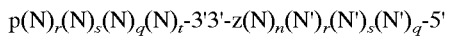

where N is a nucleotide and N' is its complement, p is a phosphate group, z is a 3' hydroxyl or a 3' blocking group, n is an integer between 2 and 6, inclusive, r is an integer greater than or equal to 0, s is an integer which is either between four and six whenever the encoded adaptor has a nuclease recognition site or is 0 whenever there is no nuclease recognition site, q is an integer greater than or equal to 0, and t is an integer between 8 and 20, inclusive. More preferably, n is 4 or 5, and t is between 9 and 15, inclusive. Whenever an encoded adaptor contains a nuclease recognition site, the region of "r" nucleotide pairs is selected so that a predetermined number of nucleotides are cleaved from a target polynucleotide whenever the nuclease recognizing the site is applied. The size of "r" in a particular embodiment depends on the reach of the nuclease (as the term is defined in U.S. Pat. No. 5,599,675) and the number of nucleotides sought to be cleaved from the target polynucleotide. Preferably, r is between 0 and 20; more preferably, r is between 0 and 12. The region of "q" nucleotide pairs is a spacer segment between the nuclease recognition site and the tag region of the encoded probe. The region of "q" nucleotide may include further nuclease recognition sites, labeling or signal generating moieties, or the like. The single stranded oligonucleotide of "t" nucleotides is a "t-mer" oligonucleotide tag selected from a minimally cross-hybridizing set.

The 3' blocking group "z" may have a variety of forms and may include almost any chemical entity that prevent inter-adaptor ligation and that does not interfere with other steps of the method, e.g. removal of the 3' blocked strand, ligation, or the like. Exemplary 3' blocking groups include, but are not limited to, hydrogen (i.e. 3' deoxy), phosphate, phosphorothioate, acetyl, and the like. Preferably, the 3' blocking group is a phosphate because of the convenience in adding the group during the synthesis of the 3' blocked strand and the convenience in removing the group with a phosphatase to render the strand capable of ligation with a ligase. An oligonucleotide having a 3' phosphate may be synthesized using the protocol described in chapter 12 of Eckstein, Editor, Oligonucleotides and Analogues: A Practical Approach (IRL Press, Oxford, 1991).

Further 3' blocking groups are available from the chemistries developed for reversable chain terminating nucleotides in base-by-base sequencing schemes, e.g. disclosed in the following references: Cheeseman, U.S. Pat. No. 5,302,509; Tsien et al, International application WO 91/06678; Canard et al, Gene, 148: 1–6 (1994); and Metzker et al, Nucleic Acids Research, 22: 4259–4267 (1994). Roughly, these chemistries permit the chemical or enzymatic removal of specific blocking groups (usually having an appendent label) to generative a free hydroxyl at the 3' end of a priming strand.

Preferably, when z is a 3' blocking group, it is a phosphate group and the double stranded portion of the adaptors contain a nuclease recognition site of a nuclease whose recognition site is separate from its cleavage site.

When double stranded oligonucleotide tags are employed that specifically hybridize with single stranded tag complements to form triplex structures, encoded tags of the invention preferably have the following form:

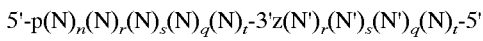

or

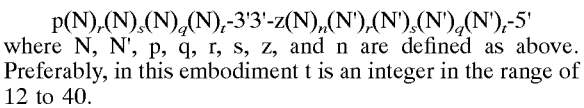

where N, N', p, q, r, s, z, and n are defined as above. Preferably, in this embodiment t is an integer in the range of 12 to 40.

Clearly, there are additional structures which contain elements of the basic designs set forth above that would be apparent to those with skill in the art. For example, encoded adaptors of the invention include embodiments with multiple tags, such as the following:

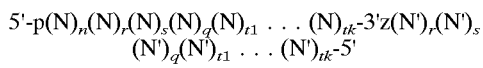

or

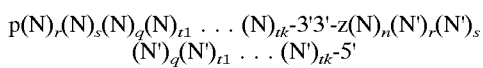

where the encoded adaptor includes k double stranded tags. Preferably, $t_1=t_2= \ldots t_k$ and k is either 1, 2, or 3.

The tag complements of the invention can be labeled in a variety of ways for decoding oligonucleotide tag, including the direct or indirect attachment of radioactive moieties, fluorescent moieties, colorimetric moieties, chemiluminescent moieties, and the like. Many comprehensive reviews of methodologies for labeling DNA and constructing DNA adaptors provide guidance applicable to constructing adaptors of the present invention. Such reviews include Matthews et al, Anal. Biochem., Vol 169, pgs. 1–25 (1988); Haugland, Handbook of Fluorescent Probes and Research Chemicals (Molecular Probes, Inc., Eugene, 1992); Keller and Manak, DNA Probes, 2nd Edition (Stockton Press, New York, 1993); and Eckstein, editor, Oligonucleotides and Analogues: A Practical Approach (IRL Press, Oxford, 1991); Wetmur, Critical Reviews in Biochemistry and Molecular Biology, 26: 227–259 (1991); and the like. Many more particular methodologies applicable to the invention are disclosed in the following sample of references: Fung et al, U.S. Pat. No. 4,757,141; Hobbs, Jr., et al U.S. Pat. No. 5,151,507; Cruickshank, U.S. Pat. No. 5,091,519; (synthesis of functionalized oligonucleotides for attachment of reporter groups); Jablonski et al, Nucleic Acids Research, 14: 6115–6128 (1986)(enzyme-oligonucleotide conjugates); Ju et al, Nature Medicine, 2: 246–249 (1996); and Urdea et al, U.S. Pat. No. 5,124,246 (branched DNA). Attachment sites of labeling moieties are not critical, provided that such labels do not interfere with the ligation and/or cleavage steps.

Preferably, one or more fluorescent dyes are used as labels for tag complements, e.g. as disclosed by Menchen et al., U.S. Pat. No. 5,188,934; Bergot et al., PCT Pubn. No. WO 91/05060. As used herein, the term "fluorescent signal generating moiety" means a signaling means which conveys information through the fluorescent absorption and/or emission properties of one or more molecules. Such fluorescent properties include fluorescence intensity, fluorescence life time, emission spectrum characteristics, energy transfer, and the like.

Attaching Tags to Restriction Fragments for Sorting onto Solid Phase Supports An important aspect of the invention is the sorting and attachment of populations of DNA fragments, e.g. from a restriction digest, to microparticles or to separate regions on a solid phase support such that each microparticle or region has substantially only one kind of fragment attached. This objective is accomplished by insuring that substantially all different fragments have different tags attached. This condition, in turn, is brought about by taking a sample of the full ensemble of tag-fragment conjugates for analysis. (It is acceptable that identical fragments have different tags, as it merely results in the same fragment being operated on or analyzed twice in two different locations.) Such sampling can be carried out either overtly—for example, by taking a small volume from a larger mixture—after the tags have been attached to the fragments, it can be carried out inherently as a secondary effect of the techniques used to process the fragments and tags, or sampling can be carried out both overtly and as an inherent part of processing steps.

If a sample of n tag-fragment conjugates are randomly drawn from a reaction mixture—as could be effected by taking a sample volume, the probability of drawing conjugates having the same tag is described by the Poisson distribution, $P(r)=e^{-\lambda}(\lambda)^r/r$, where r is the number of conjugates having the same tag and $\lambda=np$, where p is the probability of a given tag being selected. If $n=10^6$ and $p=1/(1.67\times 10^7)$ (for example, if eight 4-base words described in Brenner et al were employed as tags), then $\lambda=0.0149$ and $P(2)=1.13\times 10^{-4}$. Thus, a sample of one million molecules gives rise to an expected number of doubles well within the preferred range. Such a sample is readily obtained by serial dilutions of a mixture containing tag-fragment conjugates.

As used herein, the term "substantially all" in reference to attaching tags to molecules, especially polynucleotides, is meant to reflect the statistical nature of the sampling procedure employed to obtain a population of tag-molecule conjugates essentially free of doubles. The meaning of substantially all in terms of actual percentages of tag-molecule conjugates depends on how the tags are being employed. Preferably, for nucleic acid sequencing, substantially all means that at least eighty percent of the polynucleotides have unique tags attached. More preferably, it means that at least ninety percent of the polynucleotides have unique tags attached. Still more preferably, it means that at least ninety-five percent of the polynucleotides have unique tags attached.

Preferably, restriction fragments are conjugated to oligonucleotide tags by inserting the fragments into a conventional cloning vector carrying a tag library. For example, a pUC19 plasmid may be prepared for accepting the tag library of Formula I as follows: Into a Bam HI/Sac I-digested pUC19 the following adaptor (SEQ ID NO: 3) is ligated to introduce a Pac I site:

After the recombinant plasmid is cloned and isolated, fragments from a Sau 3A-digested target polynucleotide may be inserted into the Bam HI site to form a tag-fragment library, which includes every possible tag-fragment pairing. A sample is taken from this library for amplification and sorting. Sampling may be accomplished by serial dilutions of the library, or by simply picking plasmid-containing bacterial hosts from colonies. After amplification, the tag-fragment conjugates may be excised from the plasmid by Pac I/Xba I digestion. The residual Pac I site allows the oligonucleotide tag to be rendered single stranded by T4 DNA polymerase digestion in the presence of dGTP.

After the oligonucleotide tags are prepared for specific hybridization, e.g. by rendering them single stranded as described above, the polynucleotides are mixed with microparticles containing the complementary sequences of the tags under conditions that favor the formation of perfectly matched duplexes between the tags and their complements. There is extensive guidance in the literature for creating these conditions. Exemplary references providing such guidance include Wetmur, Critical Reviews in Biochemistry and Molecular Biology, 26: 227–259 (1991); Sambrook et al, Molecular Cloning: A Laboratory Manual, 2nd Edition (Cold Spring Harbor Laboratory, New York, 1989); and the like. Preferably, the hybridization conditions are sufficiently stringent so that only perfectly matched sequences form stable duplexes. Under such conditions the polynucleotides specifically hybridized through their tags may be ligated to the complementary sequences attached to the microparticles. Finally, the microparticles are washed to remove polynucleotides with unligated and/or mismatched tags.

Preferably, for sequencing applications, standard CPG beads of diameter in the range of 20–50 μm are loaded with about $10^5$ polynucleotides, and glycidalmethacrylate (GMA) beads available from Bangs Laboratories (Carmel, Ind.) of diameter in the range of 5–10 μm are loaded with a few tens of thousand polynucleotide, e.g. $4\times 10^4$ to $6\times 10^4$.

Specificity of the hybridizations of tag to their complements may be increased by taking a sufficiently small sample so that both a high percentage of tags in the sample are unique and the nearest neighbors of substantially all the tags in a sample differ by at least two words. This latter condition may be met by taking a sample that contains a number of tag-polynucleotide conjugates that is about 0.1 percent or less of the size of the repertoire being employed. For example, if tags are constructed with eight words a repertoire of $8^8$, or about $1.67 \times 10^7$, tags and tag complements are produced. In a library of tag-fragments conjugates as described above, a 0.1 percent sample means that about 16,700 different tags are present. If this were loaded directly onto a repertoire-equivalent of microparticles, or in this example a sample of $1.67 \times 10^7$ microparticles, then only a sparse subset of the sampled microparticles would be loaded. The density of loaded microparticles can be increase—for example, for more efficient sequencing—by undertaking a "panning" step in which the sampled tag-fragment conjugates are used to separate loaded microparticles from unloaded microparticles. Thus, in the example above, even though a "0.1 percent" sample contains only 16,700 cDNAs, the sampling and panning steps may be repeated until as many loaded microparticles as desired are accumulated. Alternatively, loaded microparticles may be separated from unloaded microparticles by a fluorescently activated cell sorting (FACS) instrument using conventional protocols after fragments have been fluorescently labeled. After loading and FACS sorting, the label may be cleaved prior to ligating encoded adaptors, e.g. by Dpn I or like enzyme that recognizes methylated sites.

A panning step may be implemented by providing a sample of tag-fragment conjugates each of which contains a capture moiety at an end opposite, or distal to, the oligonucleotide tag. Preferably, the capture moiety is of a type which can be released from the tag-fragment conjugates, so that the tag-fragment conjugates can be sequenced with a single-base sequencing method. Such moieties may comprise biotin, digoxigenin, or like ligands, a triplex binding region, or the like. Preferably, such a capture moiety comprises a biotin component. Biotin may be attached to tag-fragment conjugates by a number of standard techniques. If appropriate adapters containing PCR primer binding sites are attached to tag-fragment conjugates, biotin may be attached by using a biotinylated primer in an amplification after sampling. Alternatively, if the tag-fragment conjugates are inserts of cloning vectors, biotin may be attached after excising the tag-fragment conjugates by digestion with an appropriate restriction enzyme followed by isolation and filling in a protruding strand distal to the tags with a DNA polymerase in the presence of biotinylated uridine triphosphate.

After a tag-fragment conjugate is captured, it may be released from the biotin moiety in a number of ways, such as by a chemical linkage that is cleaved by reduction, e.g. Herman et al, Anal. Biochem., 156: 48–55 (1986), or that is cleaved photochemically, e.g. Olejnik et al, Nucleic Acids Research, 24: 361–366 (1996), or that is cleaved enzymatically by introducing a restriction site in the PCR primer.

Physical Map Construction by Partial Methylation

Figure 4:
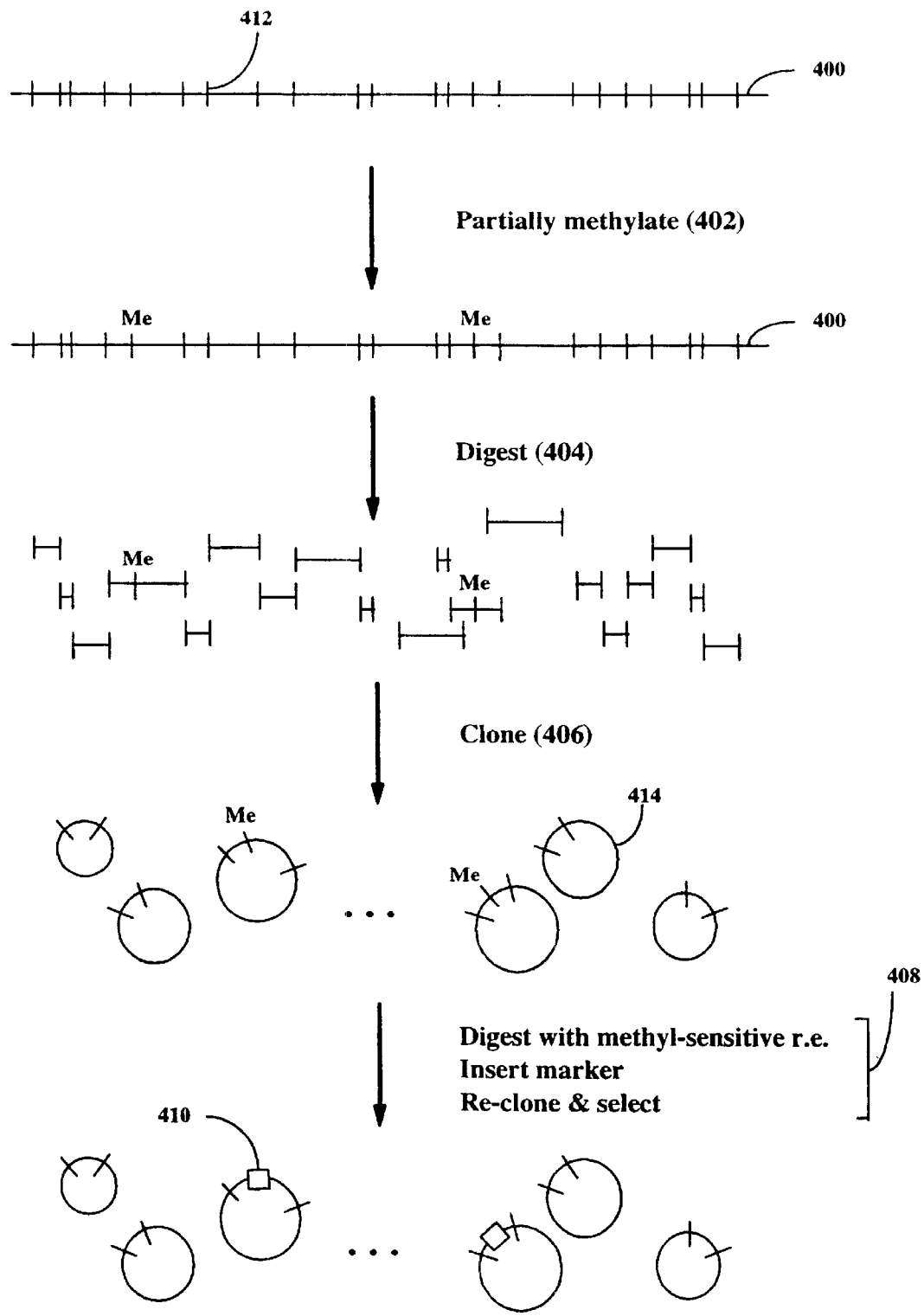
FIG. 4 illustrates an embodiment of the invention which employs partial methylation to generate cleavable fragments for sequencing.

As mentioned above, the invention may be implemented with the use of restriction enzymes which have methyl-sensitive isoschizomers, e.g. Dpn I is a methyl-sensitive isoschizomer of Mbo I, Sau 3A, and Dpn II with respect to dam methylation. That is, Dpn I is able to cleave only a GATC site which is dam-methylated, whereas Mbo I and Dpn II, which also cleave at GATC, are blocked by dam methylation. For such pairs of restriction endonucleases, ordered pairs of sequences may be prepared as shown in FIG. 4. Polynucleotide (400) contains restriction sites (412) is partially methylated (402), e.g. with a dam methylase (New England Biolabs, Beverly, Mass.), so that the likelihood of adjacent sites being methylated is low. Preferably, methylation of adjacent sites is avoided because double methylated fragments could lead to gaps or ambiguities in the reconstructed map. On the other hand, the partial methylation must be complete enough so that at least one representative of every site is present in methylated form. If sites at some positions are completely unmethylated, then a gap is created in the reconstructed map. Preferably, about 0.5 to about 2 percent of the restriction sites are methylated. Partially methylated polynucleotide (400) is digested with a restriction endonuclease which is blocked from cleaving methylated sites. The resulting fragments are cloned (406) into a conventional cloning vector carrying a repertoire of oligonucleotide tags, after which the cloning vector is expanded and fragment-containing vectors are isolated. After digestion with the methyl-sensitive isoschizomer, a marker fragment, e.g. supF or the like, is inserted into the opened site, the re-circularized vectors are cloned, plated, and selected for the presence of the inserted marker. A sufficiently large sample of marker-containing clones are harvested so that with high probability, preferably greater than 99%, all fragments of the polynucleotide are represented. Preferably, tag-containing fragments are then excised from the vectors and prepared for loading onto microparticles for sequencing, as described above.

EXAMPLE 1

Digestion and Loading Restriction Fragments from Phase λ for MPSS Analysis

In this example, aliquots of phage λ DNA are separately digested with Tsp 509 I (recognizing 5'-AATT) and Dpn II (recognizing 5'-GATC). Restriction fragments from the separate digestions are inserted into pUC19 or pUC18 plasmids containing oligonucleotide tag repertoires, thus forming a library of tag-Tsp 509 I fragment conjugates and a library of tag-Dpn II fragment conjugates. Samples of about $10^5$ clones are obtained from each library. (This is more than required to provide an adequate representation of the populations, given that the complexity of the fragment mixture is only about 100–200 for phage λ. Also, the sample size is still small enough so that it is only about 1% the complexity of the tag library described above, so there is a high probability that each fragment will receive a unique tag). After sampling, tag-fragment conjugates from the two samples are separately transfected into hosts and expanded in culture, after which the plasmids are isolated. Tag-fragment conjugates are then amplified from the plasmids by 4–5 cycles of PCR in the presence of 5-methyldeoxycytosine triphosphate using appropriate flanking vector sequences as primer binding sites. After amplification, the tags of the tag-fragment conjugates are rendered single stranded and loaded onto microparticles carrying tag complements. Dpn II and Tsp 509 I are selected for being able to cleave DNA whose deoxycytosines are methylated at the 5-carbon position.

To facilitate the initiation of sequencing after methylation, the following adaptor (SEQ ID NO: 4) is inserted into an Xba I-Sal I digested pUC19:

5'-CTAGAAGCTGCGCTTGCTTTTGTTC-
GACGCGAACGAAAACAGCT

The tag library of Formula I is digested with Eco RI and Kpn I and inserted into the modified pUC19 (New England Biolabs, Beverly, Mass.) which is similarly digested, using conventional protocols. The resulting recombinants are transfected into a suitable host (e.g. preferably, dam⁻, Stratagene, La Jolla, Calif.) and expanded in culture. Tag-pUC19 recombinants isolated from the culture are digested with Bam HI and ligated to Dpn II restriction fragments, after which the resulting recombinant products are again transfected into a host and expanded to form a library of tag-Dpn II fragment conjugates. After isolation, a sample of about $10^5$ tag-Dpn II fragment conjugates are obtained by serial dilution. The sample is re-transfected into fresh host bacteria and expanded in culture. From a standard miniprep of plasmid, the tag-Dpn II fragment conjugates are amplified by PCR with 5-methyldeoxycytosine triphosphate substituted for deoxycytosine triphosphate. The following 19-mer forward and reverse primers (SEQ ID NO: 5 and SEQ ID NO: 6), specific for flanking sequences in pUC19, are used in the reaction:

forward primer: 5'-biotin-GAATTCGGGCCTTAATTAA reverse primer: 5'-FAM-CAAAAGCAAGCGCAGCTTC where "FAM" is an NHS ester of fluorescein (Clontech Laboratories, Palo Alto, Calif.) coupled to the 5' end of the reverse primer via an amino linkage, e.g. Aminolinker II (Perkin-Elmer, Applied Biosystems Division, Foster City, Calif.). The reverse primer is selected so that a Bbv I site without methylated deoxycytosines can be reconstituted. This is accomplished by using a reverse primer whose deoxycytosines are un-methylated and by carrying out a "stripping" reaction with T4 DNA polymerase in the presence of dATP (and absent the other dNTPs).

After PCR amplification, the tag-Dpn II fragments are isolated on avidinated beads, e.g. M-280 Dynabeads (Dynal, Oslo, Norway). After thorough washing, the 3' strand in the region of the reverse primer stripped back to the initial adenosine by treatment with T4 DNA polymerase in the presence of dATP. dTTP, dCTP, and dGTP are then added to the reaction to extend back the 3' strand, thereby reconstituting the Bbv I site without methylated deoxycytosines.

After another thorough washing, the fragments bound to the beads are digested with Pac I releasing the tag-fragment conjugates and a stripping reaction is carried out to render the oligonucleotide tags single stranded. After the reaction is quenched, the tag-fragment conjugate is purified by phenol-chloroform extraction and combined with 5.5 gm GMA beads carrying tag complements, each tag complement having a 5' phosphate. Hybridization is conducted under stringent conditions in the presence of a thermal stable ligase so that only tags forming perfectly matched duplexes with their complements are ligated. The GMA beads are washed and the loaded beads are concentrated by FACS sorting, using the fluorescently labeled cDNAs to identify loaded GMA beads.

Separately from above, the following tag library is constructed for preparation of the tag-Tsp 509 conjugates (SEQ ID NO: 7 and SEQ ID NO: 8):

| | Formula II | |
|---|---|---|
| Left Primer | | Kpn I |
| 5'- AGAATTCGGGCCTTAATTAA | | ↓ |
| 5'- AGTCGACGGGCCTTAATTAA- | [⁴(A,C,T)₈]-GGGTACCAAGTCAGAGTGAT | |
| TCAGCTGCCCGG<u>AATTAATT</u>- | [⁴(T,G,A)₈]-C<u>CCATGG</u>TTCAGTCTCACTA | |
| | | CCCATGGTTCAGTCTCACTA -5' |
| ↑ | ↑ | |
| Sal I | Pac I | Right Primer |

This library is inserted into a pUC19 plasmid whose polylinker region is modified so that the upstream Eco RI site is destroyed and a new sequence of restriction sites Sal I-Kpn I-Eco RI-Apo I is inserted in place of the fragment between the Eco RI and Pst I sites of the unmodified pUC19. The modification is effected by digesting pUC19 with Eco RI and Pst I, isolating the larger fragment, and ligating the following adaptor (SEQ ID NO: 9) to the larger pUC19 fragment to form the modified pUC19:

5'-AATTTGTCGACATCTTCTCTTGGTACCGAATTCAAATTTCTGCA
    A<u>CAGCTG</u>TAGAAGAGAA<u>CCATGG</u>CT<u>TAAGTTT</u>AAAG
      ↑              ↑        ↑      ↑
     Sal I         KpnI    Eco RI  Apo I

The tag library of Formula II is digested with Sal I and Kpn I and inserted into the modified pUC19 using conventional protocols, after which the recombinants are transfected into a suitable host (e.g. preferably, damp, Stratagene, La Jolla, Calif.) and expanded in culture. Tsp 509 I fragments, which have compatible ends with Eco RI-digested DNA, are readily inserted into the Eco RI site. The Apo I site provides a starting location for sequencing once the tag-fragment conjugates are loading onto beads. The stripping reaction is not required in this case because Apo I does not contain methylated deoxycytosines and would not fortuitously cleave the fragment since the fragment has already been digested to completion with Tsp 509 I. Modified pUC19 recombinants isolated from culture are digested with Eco RI and ligated to Tsp 509 I restriction fragments, after which the resulting recombinant products are again transfected into a host and expanded to form a library of tag-Tsp 509 I fragment conjugates. After isolation, a sample of about $10^5$ tag-Tsp 509 I fragment conjugates are obtained by serial dilution. The sample is re-transfected into fresh host bacteria and expanded in culture. From a standard miniprep of plasmid, the tag-Tsp 509 fragment conjugates are amplified by PCR with 5-methyldeoxycytosine triphosphate substituted for deoxycytosine triphosphate. The following 19-mer forward and reverse primers (SEQ ID NO: 10 and SEQ ID NO: 11), specific for flanking sequences in pUC19, are used in the reaction:

forward primer: 5'-biotin-GTCGACGGGCCTTAATTAA reverse primer: 5'-FAM-ACGTACGGACGTCTTTAAA where "FAM" is as described above. After amplification, the tag-Tsp 509 fragment conjugates are attached to beads as described above, except rather than reconstituting an unmethylated Bbv I site for initiating sequencing, here the fragments only need be cleaved with Apo I to generate a 4-nucleotide protruding strand to which the first sequencing adaptor is ligated.

EXAMPLE 2

Signature Sequencing Phase λ Restriction Fragments with Encoded Adaptors

In this example the Dpn II and Tsp 509 fragments loaded onto beads are sequenced, digested with Tsp 509 I and Dpn II, respectively, and sequenced again to generate ordered pairs of sequences for constructing a physical map. Fragments which fail to cleave carry encoded adaptors which must be inactivated prior to the start of the second round of sequencing, otherwise spurious ordered pairs of sequence are obtained. This may be accomplished in several ways. For example, a restriction site may be included between the type IIs nuclease recognition site and the protruding strand of the encoded adaptor, or the type IIs site of the encoded adaptor may be treated with a methylase prior to the second round of sequencing. For encoded adaptors listed below, the type IIs nuclease recognition site is preferably activated by treating the fragments with Alu I methylase.

Beads loaded with tag-fragments conjugates are placed in an instrument for MPSS sequencing. Either two separate instruments are required for analyzing the Dpn II fragments and Tsp 509 fragments, or the analyses take place one after the other on the same machine, i.e. in this embodiment the loaded beads are not placed in the same chamber for sequencing. After loading and prior to sequencing, the FAM label is cleaved from the Dpn II fragments by Bbv I, which cleavage also leaves a protruding strand to which the first sequencing adaptor is ligated. Similarly, prior to sequencing, the FAM label is cleaved from the Tsp 509 fragments by Apo I, which cleavage likewise leaves a protruding strand to which the first sequencing adaptor is ligated. In both cases, the first sequencing adaptor carries a Bbv I site disposed on the adaptor so that Bbv I recognizing the site cleaves the fragment to expose a protruding strand of unknown fragment sequence. The encoded adaptors of the set described below are applied to these protruding strands. Three cycles of ligation, identification, and cleavage are carried out at the end of each fragment initially and after digestion with either Dpn II or Tsp 509 to give two 12-nucleotide ordered pairs of sequences for each fragment.

The top strands of the following 16 sets of 64 encoded adaptors (SEQ ID NO: 12 through SEQ ID NO: 27) are each separately synthesized on an automated DNA synthesizer (model 392 Applied Biosystems, Foster City) using standard methods. The bottom strand, which is the same for all adaptors, is synthesized separately then hybridized to the respective top strands:

| SEQ ID NO. | Encoded Adaptor |
|---|---|
| 12 | 5'-pANNNTACAGCTGCATCCCttggcgctgagg<br>pATGCACGCGTAGGG-5' |
| 13 | 5'-pNANNTACAGCTGCATCCCtgggcctgtaag<br>pATGCACGCGTAGGG-5' |
| 14 | 5'-pCNNNTACAGCTGCATCCCttgacgggtctc<br>pATGCACGCGTAGGG-5' |

-continued

| SEQ ID NO. | Encoded Adaptor |
|---|---|
| 15 | 5'-pNCNNTACAGCTGCATCCCtgcccgcacagt<br>pATGCACGCGTAGGG-5' |
| 16 | 5'-pGNNNTACAGCTGCATCCCttcgcctcggac<br>pATGCACGCGTAGGG-5' |
| 17 | 5'-pNGNNTACAGCTGCATCCCtgatccgctagc<br>pATGCACGCGTAGGG-5' |
| 18 | 5'-pTNNNTACAGCTGCATCCCttccgaacccgc<br>pATGCACGCGTAGGG-5' |
| 19 | 5'-pNTNNTACAGCTGCATCCCtgaggggatag<br>pATGCACGCGTAGGG-5' |
| 20 | 5'-pNNANTACAGCTGCATCCCttcccgctacac<br>pATGCACGCGTAGGG-5' |
| 21 | 5'-pNNNATACAGCTGCATCCCtgactccccgag<br>pATGCACGCGTAGGG-5' |
| 22 | 5'-pNNCNTACAGCTGCATCCCtgtgttgcgcgg<br>pATGCACGCGTAGGG-5' |
| 23 | 5'-pNNNCTACAGCTGCATCCCtctacagcagcg<br>pATGCACGCGTAGGG-5' |
| 24 | 5'-pNNGNTACAGCTGCATCCCtgtcgcgtcgtt<br>pATGCACGCGTAGGG-5' |
| 25 | 5'-pNNNGTACAGCTGCATCCCtcggagcaacct<br>pATGCACGCGTAGGG-5' |
| 26 | 5'-pNNTNTACAGCTGCATCCCtggtgaccgtag<br>pATGCACGCGTAGGG-5' |
| 27 | 5'-pNNNTTACAGCTGCATCCCtcccctgtcgga<br>pATGCACGCGTAGGG-5' | where N and p are as defined above, and the nucleotides indicated in lower case letters are the 12-mer oligonucleotide tags. Each tag differs from every other by 6 nucleotides. Equal molar quantities of each adaptor are combined in NEB #2 restriction buffer (New England Biolabs, Beverly, Mass.) to form a mixture at a concentration of 1000 pmol/μL.

Each of the 16 tag complements are separately synthesized as amino-derivatized oligonucleotides and are each labeled with a fluorescein molecule (using an NHS-ester of fluorescein, available from Molecular Probes, Eugene, Oreg.) which is attached to the 5' end of the tag complement through a polyethylene glycol linker (Clonetech Laboratories, Palo Alto, Calif.). The sequences of the tag complements are simply the 12-mer complements of the tags listed above.

Ligation of the adaptors to the target polynucleotide is carried out in a mixture consisting of 5 μl beads (20 mg), 3 μL NEB 10×ligase buffer, 5 μL adaptor mix (25 nM), 2.5 μL NEB T4 DNA ligase (2000 units/μL), and 14.5 μL distilled water. The mixture is incubated at 16° C. for 30 minutes, after which the beads are washed 3 times in TE (pH 8.0).

After centrifugation and removal of TE, the 3' phosphates of the ligated adaptors are removed by treating the polynucleotide-bead mixture with calf intestinal alkaline phosphatase (CIP) (New England Biolabs, Beverly, Mass.), using the manufacturer's protocol. After removal of the 3' phosphates, the CIP may be inactivated by proteolytic digestion, e.g. using Pronase™ (available form Boeringer Mannhiem, Indianapolis, Ind.), or an equivalent protease, with the manufacturer's protocol. The polynucleotide-bead mixture is then washed, treated with a mixture of T4 polynucleotide kinase and T4 DNA ligase (New England Biolabs, Beverly, Mass.) to add a 5' phosphate at the gap between the target polynucleotide and the adaptor, and to complete the ligation of the adaptors to the target polynucleotide. The bead-polynucleotide mixture is then washed in TE.

Separately, each of the labeled tag complements is applied to the polynucleotide-bead mixture under conditions which permit the formation of perfectly matched duplexes only between the oligonucleotide tags and their respective complements, after which the mixture is washed under stringent conditions, and the presence or absence of a fluorescent signal is measured. Tag complements are applied in a solution consisting of 25 nM tag complement 50 mM NaCl, 3 mM Mg, 10 mM Tris-HCl (pH 8.5), at 20° C., incubated for 10 minutes, then washed in the same solution (without tag complement) for 10 minute at 55° C.

After the four nucleotides are identified as described above, the encoded adaptors are cleaved from the polynucleotides with Bbv I using the manufacturer's protocol. After an initial ligation and identification, the cycle of ligation, identification, and cleavage is repeated three times to give the sequence of the 16 terminal nucleotides of the target polynucleotide.

Figure 3:
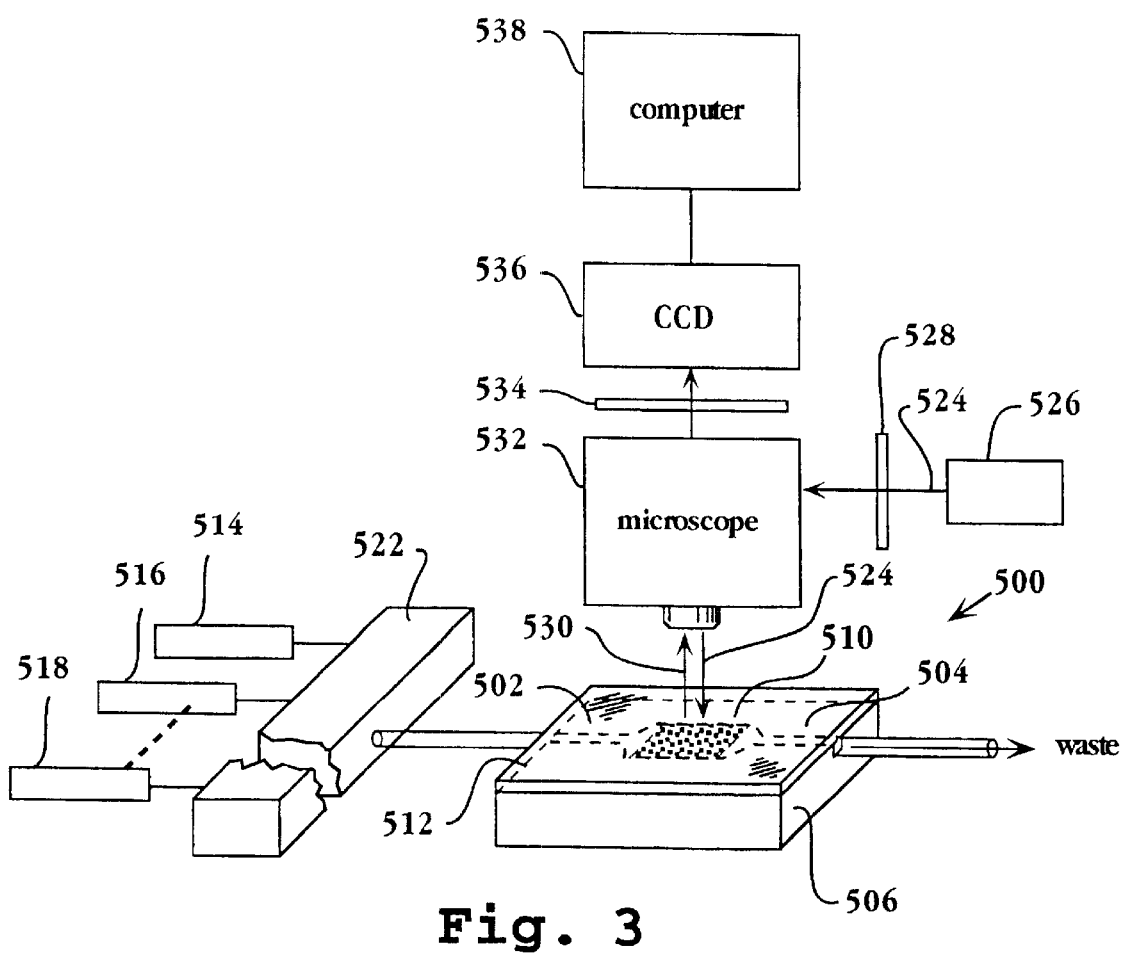
FIG. 3 is a schematic representation of a flow chamber and detection apparatus for observing a planar array of microparticles loaded with restriction fragments for sequencing.

A flow chamber (500), diagrammatically represented in FIG. 3, is prepared by etching a cavity having a fluid inlet (502) and outlet (504) in a glass plate (506) using standard micromachining techniques, e.g. Ekstrom et al., PCT Pubn. No. WO 91/16966; Brown, U.S. Pat. No. 4,911,782; Harrison et al., Anal. Chem. 64: 1926–1932 (1992); and the like. The dimensions of flow chamber (500) are such that loaded microparticles (508), e.g. GMA beads, may be disposed in cavity (510) in a closely packed planar monolayer of 100–200 thousand beads. Cavity (510) is made into a closed chamber with inlet and outlet by anodic bonding of a glass cover slip (512) onto the etched glass plate (506), e.g. Pomerantz, U.S. Pat. No. 3,397,279. Reagents are metered into the flow chamber from syringe pumps (514 through 520) through valve block (522) controlled by a microprocessor as is commonly used on automated DNA and peptide synthesizers, e.g. Bridgham et al., U.S. Pat. No. 4,668,479; Hood et al., U.S. Pat. No. 4,252,769; Barstow et al., U.S. Pat. No. 5,203,368; Hunkapiller, U.S. Pat. No. 4,703,913; or the like.

Three cycles of ligation, identification, and cleavage are carried out in flow chamber (500) to give the sequences of 12 nucleotides at the termini of each of appoximately 100,000 fragments, after which the fragments are cleaved with either Dpn II or Tsp 509 I and sequenced again. Nucleotides of the fragments are identified by hybridizing tag complements to the encoded adaptors as described above. Specifically hybridized tag complements are detected by exciting their fluorescent labels with illumination beam (524) from light source (526), which may be a laser, mercury arc lamp, or the like. Illumination beam (524) passes through filter (528) and excites the fluorescent labels on tag complements specifically hybridized to encoded adaptors in flow chamber (500). Resulting fluorescence (530) is collected by confocal microscope (532), passed through filter (534), and directed to CCD camera (536), which creates an electronic image of the bead array for processing and analysis by workstation (538). Preferably, after each ligation and cleavage step, the cDNAs are treated with Pronase™ or like enzyme. Encoded adaptors and T4 DNA ligase (Promega, Madison, Wis.) at about 0.75 units per $\mu$L are passed through the flow chamber at a flow rate of about 1–2 $\mu$L per minute for about 20–30 minutes at 16° C., after which 3' phosphates are removed from the adaptors and the cDNAs prepared for second strand ligation by passing a mixture of alkaline phosphatase (New England Bioscience, Beverly, Mass.) at 0.02 units per $\mu$L and T4 DNA kinase (New England Bioscience, Beverly Mass.) at 7 units per $\mu$L through the flow chamber at 37° C. with a flow rate of 1–2 $\mu$L per minute for 15–20 minutes. Ligation is accomplished by T4 DNA ligase (0.75 units per mL, Promega) through the flow chamber for 20–30 minutes. Tag complements at 25 nM concentration are passed through the flow chamber at a flow rate of 1–2 $\mu$L per minute for 10 minutes at 20° C., after which fluorescent labels carried by the tag complements are illuminated and fluorescence is collected. The tag complements are melted from the encoded adaptors by passing hybridization buffer through the flow chamber at a flow rate of 1–2 $\mu$L per minute at 55° C. for 10 minutes. Encoded adaptors are cleaved from the cDNAs by passing Bbv I (New England Biosciences, Beverly, Mass.) at 1 unit/$\mu$L at a flow rate of 1–2 $\mu$L per minute for 20 minutes at 37° C.

After the ordered pairs of sequences have been collected, a physical map of phage λ is constructed by matching overlapping sequences of the ordered pairs.

What is claimed is:

1. A method of ordering restriction fragments of a target polynucleotide, the method comprising the steps of:

(a) (i) producing a first population of restriction fragments by digestion of the target polynucleotide with a first restriction endonuclease having a first recognition site, (ii) attaching each restriction fragment of the first population to a solid phase support by one end, such that copies of each restriction fragment are attached to spatially discrete regions of one or more solid phase supports;

(iii) determining the nucleotide sequence of a portion of each free end of each restriction fragment of the first population;

(iv) digesting each restriction fragment of the first population with a second restriction endonuclease to form a first set of truncated support-bound restriction fragments, the second restriction endonuclease having a second recognition site different from that of the first restriction endonuclease, wherein at least one of said restriction endonucleases has a 4-basepair recognition sequence;

(v) determining the nucleotide sequence of a portion of each free end of each truncated restriction fragment of the first set, so that an ordered pair of sequences is obtained for each restriction fragment of the first population;

(b) (i) producing a second population of restriction fragments by digestion of the target polynucleotide with the second restriction endonuclease, (ii) attaching each restriction fragment of the second population to a solid phase support by one end, such that copies of each restriction fragment are attached to spatially discrete regions of one or more solid phase supports;

(iii) determining the nucleotide sequence of a portion of each free end of each restriction fragment of the second population;

(iv) digesting each restriction fragment of the second population with the first restriction endonuclease to form a second set of truncated support-bound restriction fragments;

(v) determining the nucleotide sequence of a portion of each free end of each truncated restriction fragment of the second set, so that an ordered pair of sequences is obtained for each restriction fragment of the second population; and (c) ordering the restriction fragments produced by the first and second restriction endonucleases by aligning the matching nucleotide sequences from the ordered pairs of sequences from the first and second populations of restriction fragments;

wherein each said step of attaching includes:

attaching an oligonucleotide tag from a repertoire of tags to each restriction fragment, such that each oligonucleotide tag from the repertoire is selected from the same minimally cross-hybridizing set of oligonucleotides; wherein each of said oligonucleotide tags differs from every other oligonucleotide tag of said minimally cross-hybridizing set by at least three nucleotides;

sampling said first population of restriction fragments such that substantially all different restriction fragments in said first population have different oligonucleotide tags attached; and specifically hybridizing the oligonucleotide tags with their respective tag complements, which are attached to spatially discrete regions on one or more solid phase supports;

and wherein each step of determining includes:

ligating to the free end of each support-bound restriction fragment, an encoded adaptor having a protruding strand which forms a perfectly matched duplex with said free end, said encoded adaptor further comprising an oligonucleotide tag selected from a minimally cross-hybridizing set of oligonucleotides, and a nuclease recognition site of a nuclease whose cleavage site is separate from its recognition site;

specifically hybridizing a labeled tag complement to said oligonucleotide tag of the encoded adaptor, identifying the type and sequence of nucleotides in the free end of the restriction fragment in accordance with the label carried by the tag complement;

cleaving the fragment with a nuclease recognizing the nuclease recognition site of the encoded adaptor, such that the fragment is shortened by one or more nucleotides; and repeating said ligating, hybridizing of labeled tag complements, and identifying steps, until a desired length of the nucleotide sequence of the end of the fragment is determined.

2. The method of claim 1, wherein said nucleotide sequences are at least 12 nucleotides in length.

3. The method of claim 1, wherein said target polynucleotide is between 30 and 100 kilobases in length.

4. The method of claim 1, wherein said oligonucleotide tags are single stranded.

5. The method of claim 4, wherein said tag complements are single stranded.

6. The method of claim 1, wherein each said oligonucleotide tag consists of a plurality of subunits, each subunit consisting of an oligonucleotide of 3 to 9 nucleotides in length and each subunit being selected from the same minimally cross-hybridizing set of oligonucleotides.

7. The method of claim 1, wherein said repertoire of said oligonucleotide tags contains at least 1000 of said oligonucleotide tags.

8. The method of claim 1, wherein each of said oligonucleotide tags has a length in the range of from 12 to 60 nucleotides.

9. The method of claim 1, wherein each said spatially discrete region is a microparticle.

10. The method of claim 1, wherein said repertoire contains at least 10,000 of said oligonucleotide tags.

11. The method of claim 1, wherein at least one of said one or more solid phase supports is a planar substrate having a plurality of spatially discrete surface regions.

12. The method of claim 9, wherein each said microparticle has a diameter in the range of from 5 to 40 $\mu$m.

13. The method of claim 11, wherein each of said spatially discrete surface regions has an area in the range of from 10 to 1000 $\mu m^2$.

* * * * *